US008852920B2

(12) United States Patent
Park et al.

(10) Patent No.: US 8,852,920 B2
(45) Date of Patent: Oct. 7, 2014

(54) MICRO-CHAMBER PLATE, MANUFACTURING METHOD THEREOF

(75) Inventors: Han Oh Park, Daejeon (KR); Gu-Young Song, Daejeon (KR)

(73) Assignee: Bioneer Corporation, Daejeon (KR)

( * ) Notice: Subject to any disclaimer, the term of this patent is extended or adjusted under 35 U.S.C. 154(b) by 646 days.

(21) Appl. No.: 12/743,513

(22) PCT Filed: Sep. 22, 2008

(86) PCT No.: PCT/KR2008/005635
§ 371 (c)(1),
(2), (4) Date: May 18, 2010

(87) PCT Pub. No.: WO2009/069886
PCT Pub. Date: Jun. 4, 2009

(65) Prior Publication Data
US 2010/0261184 A1    Oct. 14, 2010

(30) Foreign Application Priority Data

Nov. 30, 2007  (KR) .................. 10-2007-0124012
Mar. 5, 2008   (KR) .................. 10-2008-0020600

(51) Int. Cl.
| C12M 1/00 | (2006.01) |
| C12Q 1/68 | (2006.01) |
| C12M 1/34 | (2006.01) |
| C12P 19/34 | (2006.01) |
| C07H 21/04 | (2006.01) |
| B01L 3/00 | (2006.01) |
| G01N 21/05 | (2006.01) |
| G01N 21/64 | (2006.01) |
| G01N 21/03 | (2006.01) |

(52) U.S. Cl.
CPC ......... *B01L 3/5085* (2013.01); *B01L 3/502723* (2013.01); *B01J 2219/00662* (2013.01); *G01N 2021/054* (2013.01); *B01J 2219/00317* (2013.01); *B01L 2200/142* (2013.01); *G01N 2021/6482* (2013.01); *G01N 2021/0325* (2013.01); *B01L 2300/0867* (2013.01); *B01L 2200/16* (2013.01); *B01L 2300/0829* (2013.01); *B01L 2200/0689* (2013.01); *B01L 3/50851* (2013.01); *B01L 2200/026* (2013.01); *B01L 2200/0684* (2013.01); *G01N 21/6452* (2013.01); *B01L 2300/0887* (2013.01); *G01N 21/03* (2013.01); *G01N 2021/0346* (2013.01)

USPC ..... 435/283.1; 435/6.1; 435/91.2; 435/287.1; 435/287.2; 435/287.8; 435/288.3; 536/24.33

(58) Field of Classification Search
USPC ............... 435/6.1, 91.2, 283.1, 287.1, 287.2, 435/288.3; 536/24.33
See application file for complete search history.

(56) References Cited

U.S. PATENT DOCUMENTS

| 5,948,673 A | 9/1999 | Cottingham |
| 6,232,114 B1 | 5/2001 | Coassin et al. |
| 2003/0012693 A1* | 1/2003 | Otillar et al. ................. 422/58 |
| 2005/0272039 A1* | 12/2005 | Yasuda ........................ 435/6 |
| 2006/0024690 A1* | 2/2006 | Kao et al. ..................... 435/6 |
| 2006/0141619 A1 | 6/2006 | Hattori et al. |
| 2007/0269819 A1 | 11/2007 | Kim et al. |
| 2009/0051901 A1* | 2/2009 | Shen et al. ................... 356/73 |

FOREIGN PATENT DOCUMENTS

| EP | 1541678 A1 | 6/2005 |
| EP | 1780262 A1 | 5/2007 |
| JP | 2002245900 A | 8/2002 |
| WO | 0240158 A2 | 5/2002 |

OTHER PUBLICATIONS

Kolarz et al, Porous Structure of Copolymers Crosslinked With Multifunctional (Meth)Acrylate Monomers, 1998, Eur. Polym. J., 34, 1191-1197.*
Matsubara et al., Silicon Microchamber Array for Sequence-Specific DNA Amplification and Detection Using a Novel Dispensing Method, 7th International Conference on Miniaturized Chemical and Biochemical Analysis Systems, Oct. 5-9, 2003, pp. 745-748.
John H. Leamon et al., "A massively parallel PicoTiterPlate based platform for discrete picoliter-scale polymerase chain reactions", Electrophoresis, 2003, vol. 24, pp. 3769-3777.
Pfaffl, "Quantification strategies in real-time PCT", A-Z of quantitative PCR, Editor: S.A. Bustin, International University Line (IUL), La jolla, CA, USA, 2004.
Shipley, "An introduction to real-time PCR", Real-Time PCR, Taylor & Francis Group, edited by M. Tevfik Dorak, 2006.
Nagai et al., "Development of a Microchamber Array for Picoliter PCR", Analytical Chemistry, Mar. 1, 2001, pp. 1043-1047, vol. 73, No. 5.

* cited by examiner

*Primary Examiner* — Narayan Bhat
(74) *Attorney, Agent, or Firm* — The Webb Law Firm

(57) ABSTRACT

The present invention relates to a micro-chamber plate and a manufacturing method of the same, more precisely a micro-chamber plate facilitating real-time measurement and analysis of fluorescence obtained from the reaction of multiple reaction solutions containing primers or probes selectively binding to each corresponding gene without cross-contamination in order to analyze biological samples containing numbers of genes and a manufacturing method of the same.

16 Claims, 12 Drawing Sheets

(a)

(b)

MICRO-CHAMBER PLATE, MANUFACTURING METHOD THEREOF

TECHNICAL FIELD

The present invention relates to a micro-chamber plate and a manufacturing method of the same, more precisely a micro-chamber plate facilitating real-time measurement and analysis of fluorescence obtained from the reaction of multiple reaction solutions containing primers or probes selectively binding to each corresponding gene without cross-contamination in order to analyze biological samples containing numbers of genes and a manufacturing method of the same.

BACKGROUND ART

Micro-chamber is a container in which minute reactions of up to several micro liters occur. This micro-chamber can be composed of silicon wafer, glass, metal or plastic. Micro-chamber plate is a plate in which the said micro-chambers are arranged 2-dimensionally. In this plate, inlets for sample input are located on one side and the other side is made of a transparent material for observation of inside reaction.

To measure the amount of a gene, real-time PCR has been developed to be co-executed with polymerase chain reaction (PCR) that facilitates the measurement of fluorescence increasing in proportion to the amount of a gene.

In real-time PCR, fluorescence generated from the PCR product is measured in every cycle and a certain cycle that gives at least required fluorescence is confirmed, leading to quantification of an early concentration of a specific gene.

Real-time PCR does not require electrophoresis upon completion of PCR and is rather performed along with PCR and facilitates quantification of the product, precisely it enables quantification of a gene having a specific nucleotide sequence in the concentration range of at least $10^9$ ("A-Z of Quantitative PCR" edited by Stephen A. Bustin 2004-2006 International University, "Realtime PCR" edited by M. Tevfik Dorak 2006 Taylor & Francis Group).

Diverse devices for real-time PCR for analysis of multiple samples have been developed, which are exemplified by the apparatus analyzing 96 or 384 genes using a standard 96-well plate or 384-well plate (Roche Light cycler 480, ABI 7500, 7900).

The apparatus for real-time PCR provided by Roche requires the sample amount of 10-50 µl, which is rather a large amount.

To solve the above problem, different methods have been proposed to analyze many samples in a short period of time by reducing the amount of a sample by taking advantage of MEMS (Micro Electro Mechanical Systems) technique. One example is the method using a micro-chamber array plate.

The method using a micro-chamber array plate is composed of the following steps; loading a reaction sample in the micro-chamber; sealing each micro-chamber to isolate each reaction solution; inducing reaction and analyzing thereof.

Particularly, sample solution is added to the micro-chamber. The transparent micro-chamber plate for cell culture is covered with a semitransparent membrane to isolate micro-chambers one another. Only a cell is cultured in each micro-chamber. Then, culture medium is eliminated, to which Taqman reaction solution is added and sealed with clear oil to prevent evaporation. Fluorescence on the bottom of the plate is measured with temperature cycling (YASUDA, Kenji EP 1,541,678 A1, JP 2002245900 NUCLEIC ACID ANALYSIS CHIP AND NUCLEIC ACID ANALYZER).

According to the above method, different solutions are loaded in each micro-chamber by using a micropipette, which takes a long time. In particular, to inject samples into at least 1,536 micro-chambers, micro-automatic dispenser is necessary. This micro-automatic dispenser has to be washed after injection of each solution, which takes a long time. So, in fact, it is very difficult to use more than 384 plates.

Second, to overcome the above problem, Hdenori Nagai, a member of E. Tamiya group, proposed a reactor in which a micro-chamber array is composed of a silicon wafer by photolithography and chemical etching (Anal. Chem. 200173, 1043-1047, Development of a Microchamber Array for Picoliter PCR).

The said reactor uses microscope slide cover glass to prevent evaporation of PCR solution. But, when the cover glass is separated, there is a chance of cross contamination of the reaction solution. So, a water-repellent membrane is inserted in between the cover glass and a wafer. Then, the cover glass is eliminated first, and the water-repellent membrane is eliminated after drying the reaction solution, followed by analyzing. The above processes are troublesome. So, usability of this reactor for real-time gene quantitative amplification is limited.

Third, to overcome the problem according to the above quantitative amplification, Y. Matsubara et al of the same lab developed a micro-chamber array which was prepared by the steps of loading each primer in concave micro-chambers on a wafer using a microarray device; and drying thereof (7th International Conference on Miniaturized Chemical and Biochemical Analysis Systems Oct. 5-9, 2003, Squaw Valley Calif. USA).

In this micro-chamber array, the upper part of the chip is covered with mineral oil to seal the micro-chamber completely, and then PCR reaction mixture is loaded on the mineral oil using a nano-jet dispenser. According to this method, 1,248 micro-chamber array chips having the volume of nano liter (0.65×0.65×0.2 mm) are prepared with a silicon wafer (1×3 inch) by photolithography and chemical etching. Primers and Taqman probe solution are distributed in the micro-chamber using a nano-liter dispenser, followed by drying. The whole chip is coated with mineral oil and thus each micro-chamber is separated and sealed.

The micro-chamber array prepared according to the third method above is advantageous for PCR without cross-contamination among reaction components. Particularly, according to this method, a mixed solution of Taq DNA polymerase and sample DNA is sprayed on top of the mineral oil, which is distributed in each micro-chamber, leading to PCR of each reaction component in the micro-chamber without cross-contamination.

However, the above method also has problems as follows. The method requires a microarray nano-liter dispenser for injection of a solution. Distribution takes a long time. And there is high possibility of cross-contamination among reaction solutions owing to the flow of mineral oil during moving the plate. In addition, bubbles are formed at high temperature during temperature cycling. And lens effect resulted from hydrophobicity of oil and aqueous solution that changes aqueous solution into a spherical shape is another problem which causes scattering and dispersion of excitation light and emitting light during optical measurement, making measurement error bigger.

Forth, PicoTiterPlate facilitating much more reactions than the third example above although the micro-chamber was also prepared by chemical etching like the third example was developed (John H. Leamon et al., A massively parallel Pico- TiterPlate based platform for discrete pico-liter-scale polymerase chain reactions. Electrophoresis 2003, 24, 3769-3777).

According to this method, 300,000 independent PCR reactions occur at the same time with the amount of 39.5 pl.

But, this method requires a carrier for the fixation of primers/probes, which makes it inappropriate for real-time quantitative PCR asking even optical characteristics.

Fifth, 'film reactor (or DNA card)' was proposed (U.S. Pat. No. 5,948,673) to react micro-samples.

The film reactor is composed of three layers of thin films. Precisely, the lower layer film forms the bottom of the reactor, the middle layer film forms the side of the reactor and the upper layer film forms the sample inlets. After injecting micro sample solution using a pipette, the inlets have to be completely sealed for reaction. If the inlets are not completely sealed, the reaction mixture might be evaporated during PCR. To treat thousands of samples simultaneously, the said film reactor necessarily becomes so complicated. So, this reactor is hardly applied in reality.

Sixth, a reaction plate having a standard ELISA plate size and facilitating 1,536 fluorescence analysis reactions, was described in WO 02/40158 and U.S. Pat. No. 6,232,114.

As for the plate, multiple holes are penetrated in the plate and a transparent film with weak fluorescence is attached on the plate, forming multiple reaction vessels.

Reagent is loaded in the vessels, and the vessels are sealed with a transparent film, followed by reaction. This reaction plate has clear upper and lower parts. Excitation light is irradiated on one side and fluorescence is measured on the other side.

However, this sixth example also has problems. To analyze numbers of genes, different primers and probes have to be loaded in each micro-chamber. That is, thousands of different solutions have to be injected into such minute micro-chambers for analysis of numbers of samples. So, a special equipment like a nano-liter dispenser is required and the task takes a long time. In addition, high chance of malfunction of sample injection is another problem. Since the micro-chamber cannot be completely filled with the reaction mixture, water vapor is generated on the top of the micro-chamber during temperature rise, resulting in the difficulty in optical measurement.

Therefore, a novel micro-chamber plate is required which facilitates injection of samples in multiple micro-chambers evenly, excludes cross-contamination among reaction solutions, prevents bubble formation and water vapor condensation on the side of optical measurement, and thus facilitates real-time analysis of lights generated from the reaction products.

DISCLOSURE

Technical Problem

To overcome the above problems, it is an object of the present invention to provide a micro-chamber plate facilitating accurate analysis with a small amount of sample, which is characterized by that evaporation of the reaction solution from micro-chambers for real-time PCR, homoiothermal enzyme reaction or LCR (ligase chain reaction) is prevented; injection of solution becomes easy with reducing injection time significantly; mixing between reaction solutions in different micro-chambers is prevented; and micro bubbles in the reaction solution are discharged for accurate measurement of optical values, and a manufacturing method thereof.

Technical Solution

The micro-chamber plate of the present invention is composed of a body having an optical measurement part enabling optical measurement on one side and an inlet part made for sample injection on the other side and micro-chambers having multiple spaces; a transparent layer to seal the optical measurement part on one side of the body; and an injection layer for injection of reagents including samples into the micro-chamber with blocking the inlet part of the other side.

The micro-chamber herein is characterized by that analyzing reagents containing a specific component (A) such as a primer or a probe for nucleic acid analysis are loaded before the injection layer is formed. The said micro-chamber additionally includes nucleic acid amplification enzyme, dNTP or buffer.

The said injection layer (130) is sealed with an adhesive film, a water-based envelope forming component, oil or a solid component which is a solid at room temperature upon completion of injection of common reagents containing samples.

The injection layer is composed of a punchable film. That is, the injection layer is characterized by being punched for the connection with each micro-chamber. The preferable number of holes is 1-10 per each micro-chamber.

The injection layer is also characteristically prepared by a porous material.

The transparent layer is prepared by a material not transformed at the temperature of 0° C.-100° C. and this transparent layer lets or blocks a specific wavelength light pass through.

On the micro-chamber plate, the protrusion of the inlet part area of the body makes an open space on the upper part and reagents or samples are directly loaded into the open space of the upper part of the micro-chamber.

The micro-chamber plate is also characterized by that a supply part through which common reagents containing samples are loaded is formed on one side and a sample supply layer is additionally formed thereon to discharge gas through the sealed open space.

The micro-chamber is preferably cylindrical or rectangular parallelepiped, but not always limited thereto. The size of the micro-chamber is preferably 0.3-3 mm in width and 0.5-5 mm in depth.

The micro-chamber plate is put in a separate container harboring common reagents containing samples in order for the reagents containing samples to be loaded in the micro-chamber.

The micro-chamber plate is characteristically composed of the first protection part protecting the transparent layer or the second protection part protecting the injection layer. The first protection part or the second protection part is prepared by a separable adhesive film or an attachable material.

The micro-chamber plate is characteristically constructed with multiple micro-chambers.

The manufacturing method of the micro-chamber plate of the present invention is composed of the following steps: a) preparing the body having the optical measurement part formed on one side for optical measurement and the inlet part on the other side for sample injection and micro-chambers distinguished one another by multiple open spaces (Sa); b) forming the transparent layer on the optical measurement part on the body (Sb); c) distributing the specific component (A) through the inlet part on the body to load different specific components (A) into each of the micro-chamber plates (Sc); and d) forming the injection layer on the other side of the micro-chamber plate (Sd).

The manufacturing method of the micro-chamber plate can additionally include the following step: e) forming the first protection part protecting the injection layer or the second protection part protecting the transparent layer (Se) after d) forming the injection layer (Sd).

The method for analyzing samples using the micro-chamber plate of the present invention uses the micro-chamber plate prepared by the above manufacturing method and precisely comprises the following steps: i) injecting common reagents containing samples into the micro-chamber through the injection layer of the plate (Si); ii) sealing the upper part of the injection layer upon completion of the injection of common reagents containing samples (S ii); and iii) reacting the common reagents containing samples with the specific components (S iii). In this method, sealing the upper part of the injection layer can be omitted according to the material forming the injection layer.

In the step of injecting common reagents containing samples (Si), the injection of common reagents containing samples into the micro-chamber is performed under the effect of centrifugal force and under reduced or increased pressure for efficient injection.

In the step of injecting common reagents containing samples (Si), if multiple samples or reagents are injected stepwise, the step of regulating the pressure of the micro-chamber plate (Siv) is additionally included in between each injection.

The step of regulating pressure (Siv) consists of the processes of cancellation of reducing pressure or increasing pressure to discharge remaining air bubble from the micro-chamber.

In the step of sealing (Sii), the sealing of the injection layer is performed using an adhesive film, a water-based envelope forming component, oil or a solid component which is a solid at room temperature upon completion of injection of common reagents containing samples.

Advantageous Effects

The micro-chamber plate of the present invention and the manufacturing method of the same can reduce the amount of reaction solution since the method requires only a small amount of sample and reduce time for analysis since temperature regulation is easy because the micro-chamber plate is thin and increases accuracy of analysis by preventing solutions in separate micro-chambers from being contaminated by contacting one another and by preventing air bubble generated in the micro-chamber from remaining therein with causing inaccurate measurement of optical measurement.

The micro-chamber plate of the present invention and the manufacturing method of the same also have advantages of easy injection of sample solution into the micro-chamber which facilitates simultaneous treatment of a large amount of samples and simple treatment processes which makes the analysis procedure simple and easy.

In addition, according to the present invention, multiple micro-chamber plates are formed as one body but each micro-chamber plate can have different reagents, so that simultaneous comparison and analysis of a large amount of samples can be performed in a shorter period of time.

DESCRIPTION OF DRAWINGS

The above and other objects, features and advantages of the present invention will become apparent from the following description of preferred embodiments given in conjunction with the accompanying drawings, in which.

DESCRIPTIONS OF MARKS INDICATED IN MAJOR PARTS OF FIGURES

Figure 1:
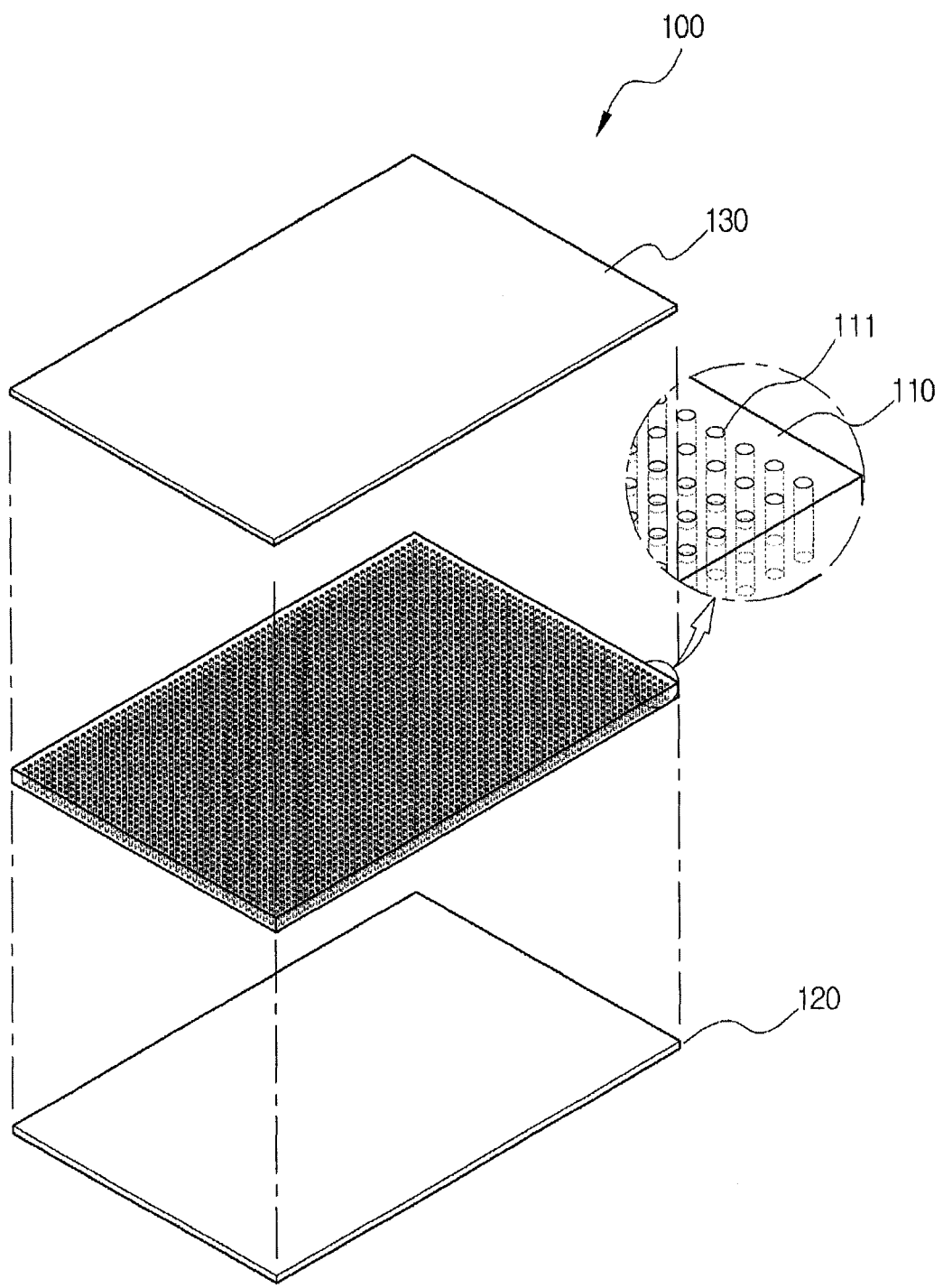
FIG. 1 is a skew drawing illustrating the micro-chamber plate of the present invention.

1000: analysis system for real-time PCR of the present invention
100: micro-chamber plate
110: body,
111: micro-chamber
$L_{111}$: width of micro-chamber
$D_{111}$: depth of micro-chamber
112: inlet part,
113: optical measurement part
114: open space part,
115: partition wall part
120: transparent layer
130: injection layer
140: sample supply layer,
141: supply part
150: first protection part
160: second protection part
170: body connection part
200: pressure regulating device,
300: temperature regulating device
400: rotating device
A: specific component
Sa~Se: each step of the manufacturing method of the micro-chamber plate of the present invention Si~Siv: analysis method using the micro-chamber plate of the present invention

BEST MODE

The micro chamber plate (100) of the present invention and the manufacturing method of the same are described in detail hereinafter with Figures attached.

Figure 2:
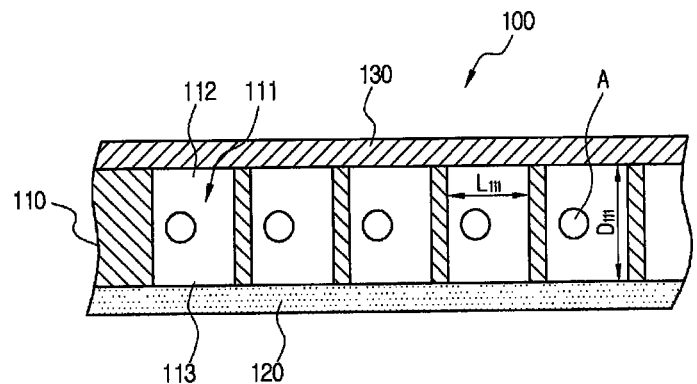
FIG. 2 is a section drawing illustrating the micro-chamber plate shown in FIG. 1.
Figure 3:
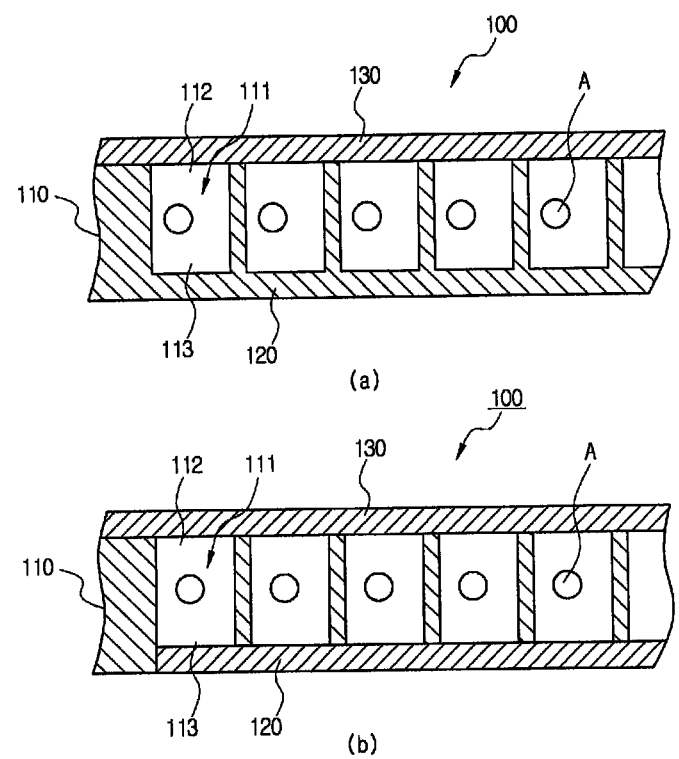
FIG. 3 is another section drawing illustrating the micro-chamber plate of the present invention.
Figure 4:
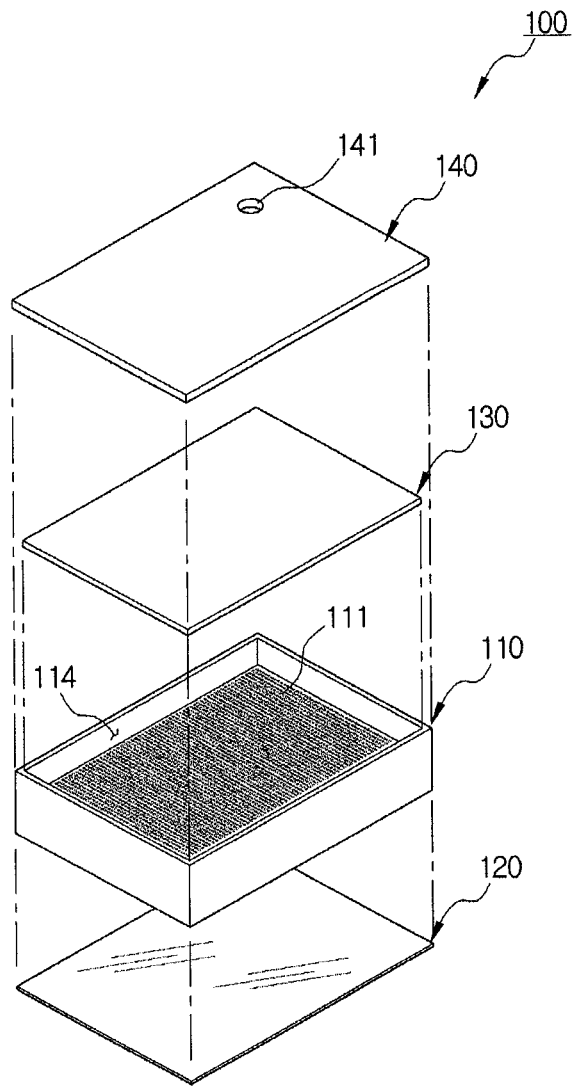
FIG. 4 is another skew drawing illustrating the micro-chamber plate of the present invention.
Figure 5:
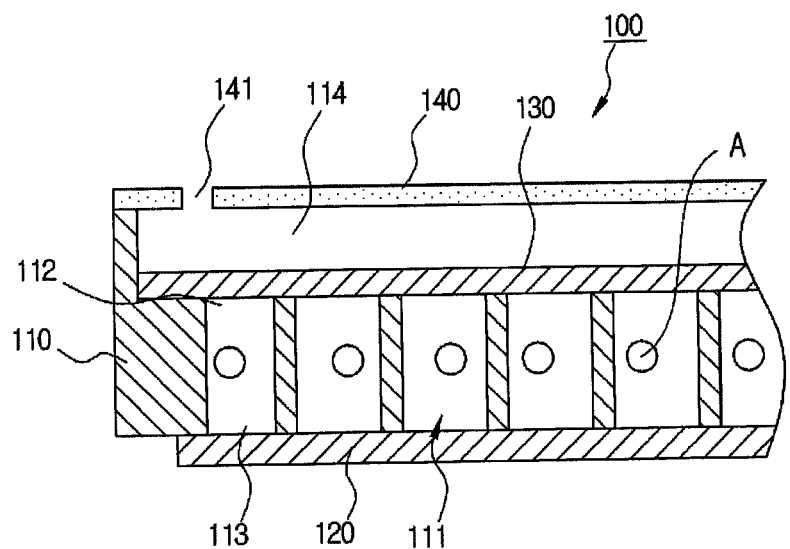
FIG. 5 is a section drawing illustrating the micro-chamber plate shown in FIG. 4.
Figure 6:
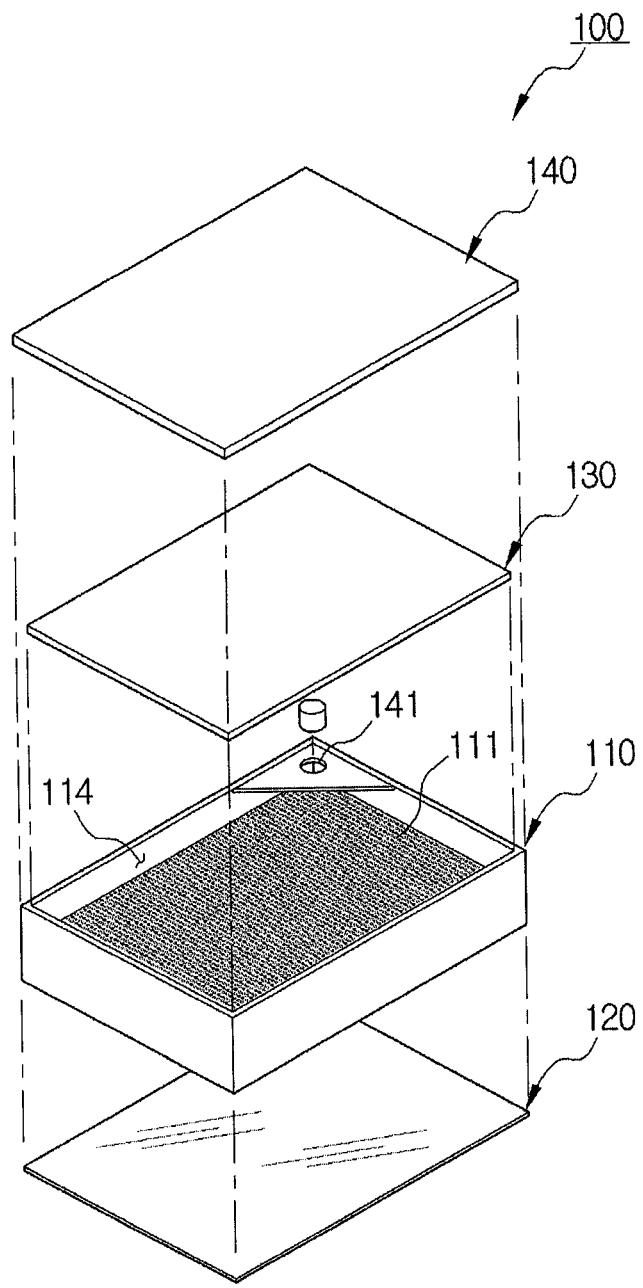
FIG. 6 is another skew drawing illustrating the micro-chamber plate of the present invention.
Figure 7:
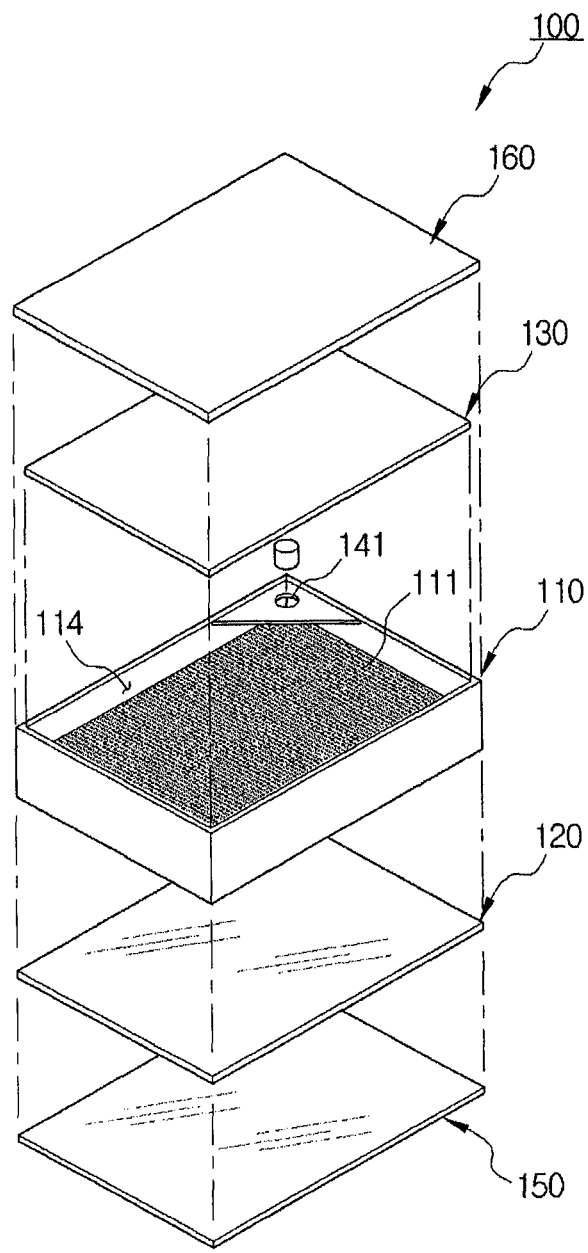
FIG. 7 is another skew drawing illustrating the micro-chamber plate of the present invention.
Figure 8:
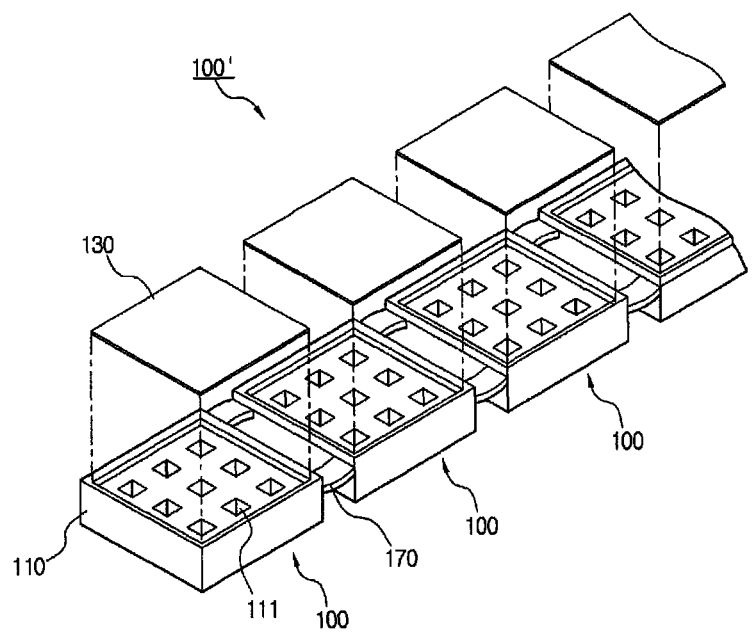
FIG. 8 is another skew drawing illustrating the micro-chamber plate of the present invention.
Figure 9:
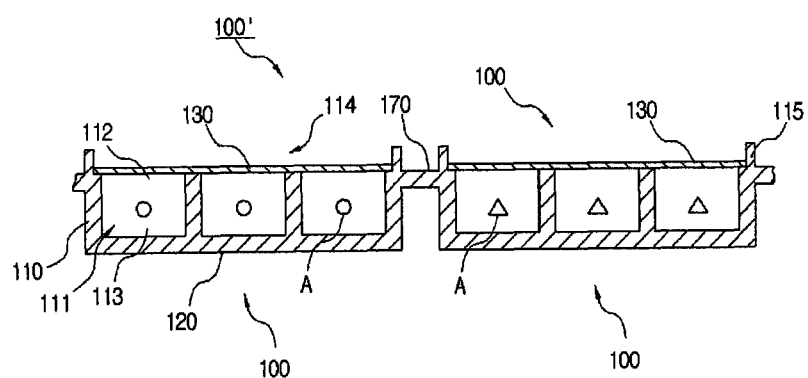
FIG. 9 is a section drawing illustrating the micro-chamber plate shown in FIG. 8.
Figure 10:
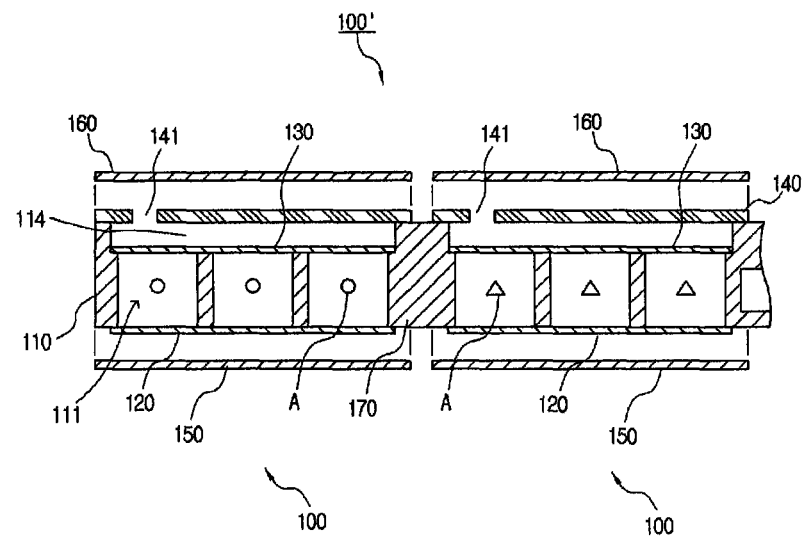
FIG. 10 is another section drawing illustrating the micro-chamber plate of the present invention.
Figure 11:
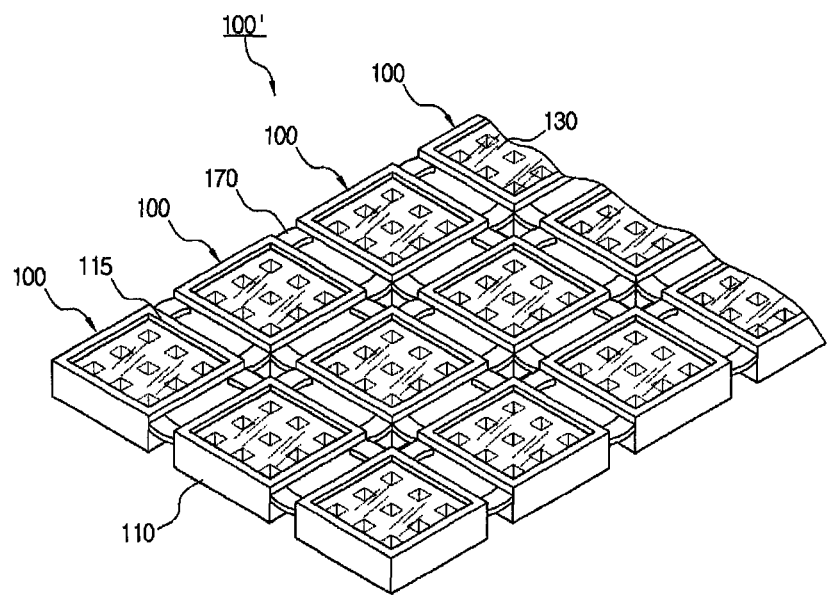
FIG. 11 is another skew drawing illustrating the micro-chamber plate of the present invention.

FIG. 1 is a skew drawing illustrating the micro-chamber plate (100) of the present invention, FIG. 2 is a section drawing illustrating the micro-chamber plate (100) shown in FIG. 1, FIG. 3 is another section drawing illustrating the micro-chamber plate (100) of the present invention, FIG. 4 is another skew drawing illustrating the micro-chamber plate (100) of the present invention, FIG. 5 is a section drawing illustrating the micro-chamber plate (100) shown in FIG. 4, FIG. 6 and FIG. 7 are other skew drawings illustrating the micro-chamber plate (100) of the present invention, FIG. 8 is another skew drawing illustrating the micro-chamber plate of the present invention, FIG. 9 is a section drawing illustrating the micro-chamber plate shown in FIG. 8, FIG. 10 is another section drawing illustrating the micro-chamber plate of the present invention, and FIG. 11 is another skew drawing illustrating the micro-chamber plate of the present invention.

FIG. 1-FIG. 6 are diagrams illustrating the micro-chamber plate (100) of the present invention. The micro-chamber plate (100) of the present invention is composed of a body (110) comprising multiple micro-chambers (111) having an optical measurement part (113) and an inlet part (112); a transparent layer (120) each formed on each side of the body (110); and an injection layer (130).

The body (110) is the basic structure forming the micro-chamber plate (100), which comprises multiple micro-chambers (111) where samples, reaction solutions or solvents are loaded.

The body (110) can be prepared by silicon wafer, glass, metal or plastic. The micro-chamber (111) has an optical measurement part (113) formed on one side of the chamber to facilitate optical measurement and an inlet part (112) formed on the other side through which necessary materials for analysis are loaded.

The transparent layer (120) is to seal one side of the body (110) where the optical measurement part (113) is formed and is preferably prepared by a transparent material for optical measurement.

The micro-chamber plate (100) herein is heated during analysis. So, the plate is preferably prepared by a material having heat-resistance. The transparent layer (120) is preferably prepared by a material not to be changed at 0° C.-100° C.

The transparent layer (120) blocks a specific wavelength of light for optical measurement or allows a specific wavelength of light alone, suggesting that the transparent layer is designed to be useful for more accurate optical measurement.

The injection layer (130) is formed on the side of where the inlet part (112) is formed on the body (110) to block the inlet part (112). Common reagents containing samples are loaded through the injection layer (130) into the micro-chamber (111).

The injection layer (130) prevents the inside materials from being evaporated by blocking the inlet part (112) and is preferably prepared by a punchable material or a porous material to load reagents into the micro-chamber (111).

The punchable material can be a film type material and the film type injection layer (130) is punched to connect with the micro-chamber (111).

The number of holes is 1-10 per micro-chamber (111). A material for the film is selected from the group consisting of Teflon, polypropylene, polyethylene, polyester, PVC and PET. The width of the hole is 10 μm-1 mm, and more 100-500 μm.

It is more preferred to regulate pressure for successful injection through the injection layer (130).

The injection layer (130) can be used as the porous material itself without punching. The porous material herein is exemplified by microporous membrane, mesh type material, and non-woven fabric. The pore size of the porous material is preferably 0.1-100 μm.

Upon completion of the injection of samples through the injection layer (130), the injection layer (130) is covered with an adhesive film, a water-based envelope forming component, oil or a solid component which is a solid at room temperature to prevent evaporation or discharge of samples and to prevent mixing among samples in different micro-chambers (111). If the injection layer (130) is made of a punchable film material, the upper part of the injection layer (130) is preferably covered with an adhesive film tape such as vinyl tape. If the injection layer (130) is made of a porous material, the injection layer (130) is smeared with mineral oil (Sigma) now being sold for PCR in order to penetrate the oil component through the injection layer (130).

The micro-chamber plate (100) of the present invention can additionally contain a specific component (A) such as a fluorescence analysis reagent containing a primer or a probe for nucleic acid analysis in its micro-chambers (111) before forming the injection layer (130) and if necessary, it can additionally contain nucleic acid amplification enzyme, dNTP, buffer or a stabilizer (a material being mixed well with reaction solution, primer and enzyme to stabilize thereof and reduce adhesion onto the container, which can be exemplified by polyol, carbohydrate, bovine albumin and PEG). The specific component (A) is used as dried phase, half-dried or liquid phase according to its composition.

So, the micro-chamber (111) whose one side is sealed after the transparent layer (120) is formed contains a sample specific component (A). That is, a material having a unique function is pre-loaded before the injection layer (130) is formed, leading to the production of the micro-chamber plate.

To analyze samples with the micro-chamber plate, common reagents containing samples are injected into the micro-chambers (111) by centrifugal force or under reduced or increased pressure (illustrated in detail hereinafter).

Examples of the micro-chamber plate (100) of the present invention are illustrated in Figures.

FIG. 1 and FIG. 2 illustrate the micro-chamber plate composed of multiple micro-chambers (111) having circular cross-section in the regular intervals ($L_{111}$) on the body (110), in which the injection layer (130) and transparent layer (120) are attached separately from the body (110).

The micro-chamber (111) has the width of 0.3-3 mm ($L_{111}$) and has the depth of 0.5-5 mm ($D_{111}$). The micro-chamber plate (100) of the present invention can have a huge number of micro-chambers, suggesting that simultaneous analysis of a large amount of samples can be performed. In addition, the depth ($D_{111}$) is rather shallow, suggesting that it can have high heat-conductivity which reduces time for analysis but increases accuracy in analysis.

In fact, 24,576 micro-chambers (111) of 0.3-2.25 mm in width ($L_{111}$) can be formed on the body (110) of a standard 80×125 mm plate, which is appropriate for the reaction of micro sample of 0.1-5 μm. So, the micro-chamber plate (100) of the present invention is characterized by simultaneous quantitative analysis of a large number of genes with small amount of reaction solution.

FIG. 3 is a section drawing illustrating another example of the micro-chamber plate (100) of the present invention. In the micro-chamber plate (100) shown in FIG. 3(a), the body (110) and the transparent layer (120) are integrated, which omits the process of forming a separate transparent layer (120). Although the transparent layer (120) and the body (110) are integrated, the transparent layer (120) has to be formed appropriately for optical measurement.

In FIG. 3(b), a stepped structure is formed on the side of the body (110) where the optical measurement part (113) is formed and the transparent layer (120) is formed on the stepped region. During the generation of the transparent layer (120), cautions are needed not to generate projections.

The micro-chamber plate (100) of the present invention can have different types of sections in various figures such as square, pentagon, etc, in addition to circular form proposed in the above Figure in its micro-chambers (111) and the width ($L_{111}$) can also be modified upward or downward.

Common reagents containing samples can be loaded into the micro-chamber (111) of the micro-chamber plate (100) having the injection layer (130) formed thereon by diverse methods.

First, the micro-chamber plate (100) itself is put in the container filled with common reagents containing samples for loading.

Second, the micro-chamber plate (100) of the present invention has the open space (114) in the upper part by projection of the inlet part (112) area of the body (110) and the sample supply layer (140) is additionally generated. So, common reagents containing samples are directly provided into the open space (114).

Third, as shown in FIG. 4 and FIG. 5, this micro-chamber plate has the supply part (141) on one side through which common reagents containing samples are provided and the sample supply layer (140) is formed to block the open space (114). So, after forming the sample supply layer (140), common reagents containing samples are loaded in the upper part of the injection layer (130) through the supply part (141) and delivered into each micro-chamber (111).

Forth, as shown in FIG. 6, the sample supply layer (140) is formed as described in the above third example, but the supply part (141) is located on one side of the body (110).

In the case that the sample supply layer (140) is additionally formed, common reagents containing samples can be protected and the amount of supply can be regulated precisely, resulting in the protection effect of the injection layer (130).

The sample supply layer (140) is made of such material that does not discharge common reagents containing samples but discharge gas generated inside, so the sample supply layer plays a role in preventing discharge of common reagents containing samples and in discharging remaining air bubble from the micro-chamber (111).

If air bubble remains in the micro-chamber (111), light is dispersed by the remaining air bubble, resulting in the decrease of accuracy of optical measurement. The micro-chamber plate (100) of the present invention is designed to discharge remaining air bubble from the micro-chamber (111), so that it is advantages in overcoming the conventional problems.

The micro-chamber plate (100) can be used not only for real-time PCR but for homoiothermal enzyme reaction or LCR (ligase chain reaction). Its application can be extended by modifying the specific component (A) loaded in the micro-chamber plate.

FIG. 7 illustrates another example of the micro-chamber plate (100) of the present invention. The micro-chamber (111) can be transported if necessary and it can additionally have the first protection part (150) to protect the transparent layer (120) and the second protection part (160) to protect the injection layer (130).

The first protection part (150) and the second protection part (160) can be multiple numbers if necessary. In the case that the sample supply layer (140) is additionally formed, the second protection part (160) is formed on the upper part of the injection layer (130) or the sample supply layer (140).

The first protection part (150) is made of a separable adhesive film or an attachable material for optical measurement. The second protection part (160) can be made of an adhesive film to prevent discharge of inside solution and to prevent contamination. As a protective film, an adhesive film that has a proper strength to protect basal membrane from being damaged and is easily separated without damaging the basal membrane and does not leave impurities when it is separated is preferably used. Lid for plate can be used as the attachable material.

FIG. 8-FIG. 11 illustrate examples of the multi micro-chamber plates (100) of the present invention. The multi micro-chamber plates are included in the scope of the micro-chamber plate of the present invention. For better understanding, when one unit micro-chamber plate (100) is formed plurally and combined together, it is called the multi micro-chamber plate (100') and represented by the drawing mark 100'.

As shown in FIG. 8 and FIG. 9, the multi micro-chamber plate (100') of the present invention is composed of multiple micro-chamber plates (100) each comprising a body (110) having multiple micro-chambers (111) each containing an optical measurement part (113), an inlet part (112); a transparent layer (120) formed each side of the body (120); and an injection layer (130).

The multi micro-chamber plate (100') composed of plural micro-chamber plates (100) also has the same characteristics as the micro-chamber plate (100) has, which are illustrated hereinafter with figures for references As shown in FIG. 8 and FIG. 9, the multi micro-chamber plate (100') is equipped with the body connection part (170) connecting the neighboring micro-chamber plate (100) onto where the injection layer (130) is formed on the body (110). And herein, the transparent layer (120) and the body (110) are integrated. The body connection part (170) is not limited in shape to connect the body connection part (170) to the neighboring micro-chamber plate (100).

The multi micro-chamber plate (100') is prepared by integrating multiple micro-chamber plates (100). That is, the micro-chamber plate (100) is functioning as a unit. Each micro-chamber plate of the multi micro-chamber plate (100') contains 4-16 micro-chambers (111) and the multi micro-chamber plate contains 8-96 micro-chamber plates (100).

Each micro-chamber plate (100) forming the multi micro-chamber plate (100') contains a specific component (A) and is provided with different common reagents through the injection layer (130). It is preferred that each micro-chamber plate (100) of the multi micro-chamber plate (100') has the open space (114) on the upper part by projection of the inlet part (112) area. So, common reagents containing samples are directly provided into the open space (114) formed on the upper part of the injection layer (130).

To form the open space (114), as shown in FIG. 8 and FIG. 9, the partition wall part (115) protruded to the top of the inlet part (112) of the body (110) can be produced.

FIG. 8 and FIG. 9 illustrate examples of the micro chambers (111) loaded with same specific component (A) in their micro-chamber plates (100), in which the partition wall part (115) and the body (110) are integrated. One partition wall part (115) can be equipped to divide the micro-chamber plates (100), which can be in diverse forms as long as it can form open space for injection of reagents into each micro-chamber plate (100).

That is, the multi micro-chamber plate (100') of the present invention has an advantage of simultaneous analysis of different samples by loading a specific component (A) in the micro-chamber (111) of the body (110) and at this time every micro-chamber plate (100) is loaded with different specific components (A).

As shown in FIG. 10, the multi micro-chamber plate (100') of the present invention is composed of the multiple microchambers (111) containing a specific component (A) in the body (110) whose sides are open. The transparent layer (120) is formed on one side and the injection layer (130) is formed on the other side.

The micro-chamber plate (100) of the present invention has the open space (114) in the upper part by projection of the inlet part (112) area of the body (110) and the sample supply layer (140) is additionally generated to block the open space (114). So, common reagents are directly provided into the open space (114).

In the sample supply layer (140), the supply part (141) can be formed to provide samples. The open space (114) can be generated by the protrusion of one side of the body connection part (170).

FIG. 10 illustrates the generation of the first protection part (150) protecting the transparent layer (120) and the second protection part (160) protecting the sample supply layer (140).

FIG. 8-FIG. 10 illustrate examples of the micro-chamber plates (100) connected in line. As shown in FIG. 11, the multi micro-chamber plate (100') of the present invention can have multiple micro-chamber plates (100) connected in lines.

The multi micro-chamber plate (100') has the open space (114) on top of the inlet part (112) by protrusion of the inlet part area of the body (110) through which different reagents can be loaded and is characteristically capable of one-time analysis with diverse samples by injecting common reagents or samples directly into the open space (114) formed on top of the inlet part (130) to deliver the samples into the microchamber (111) at last.

The analysis system for real-time PCR of the present invention (1000) is characterized by using the micro-chamber plate (100) having the characteristics described above.

Figure 12:
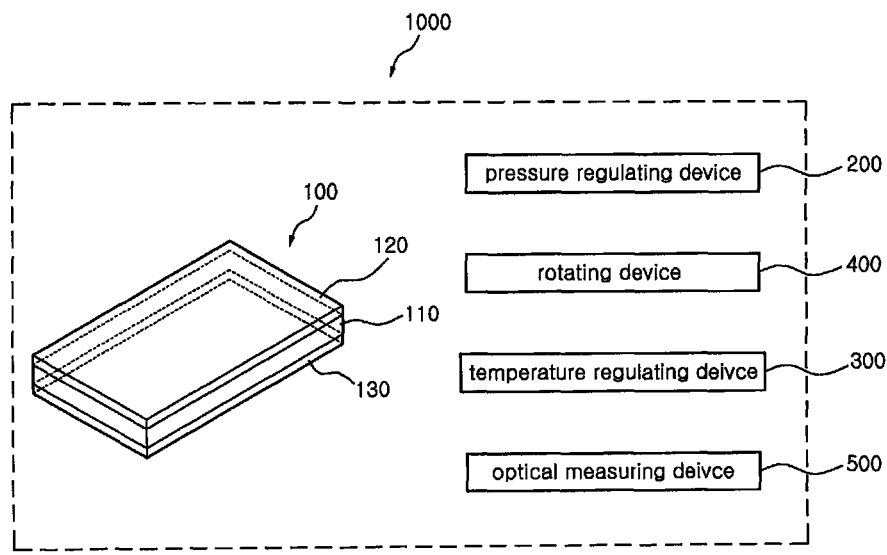
FIG. 12 is a diagram showing the analysis system for real-time PCR of the present invention.

FIG. 12 is a diagram illustrating the analysis system for real-time PCR (1000) of the present invention. As shown in FIG. 12, the analysis system for real-time PCR (1000) is equipped with the pressure regulating device (200) or the rotating device (400) and can be equipped additionally with the temperature regulating device (300) or the optical measuring device (500).

Figure 13:
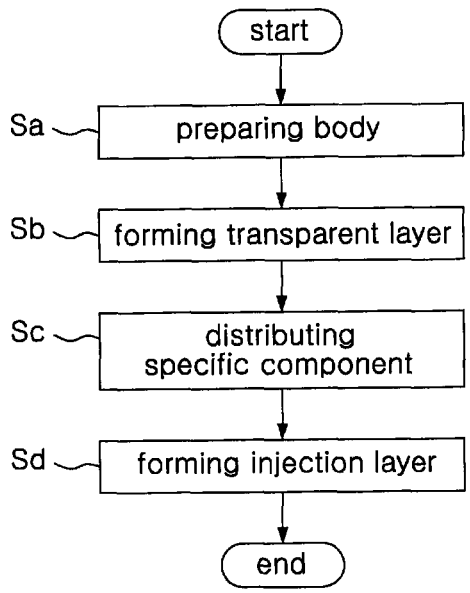
FIG. 13 is a flow chart showing the manufacturing method of the micro-chamber plate of the present invention.

FIG. 13 is a floe chart illustrating the manufacturing method of the micro-chamber plate (100) of the present invention. The manufacturing method of the micro-chamber plate (100) of the present invention is composed of the following steps: a) preparing the body (110) (Sa); b) forming the transparent layer (120) (Sb); c) distributing the specific component (A) (Sc); and d) forming the injection layer (130) (Sd).

In the step of a) preparing the body (110) (Sa), the optical measurement part (113) is formed on one side for optical measurement and the inlet part (112) is generated on the other side for sample injection and the micro-chambers (111) divided by multiple open spaces are also formed on the body (110).

In step b), the transparent layer (120) blocking the optical measurement part (113) area of the body (110) is formed. According to the preparation conditions, the body (110) preparing step (Sa) and the transparent layer (120) forming step (Sb) can be united and executed as one procedure.

In the step of c) distributing a specific component (A) (Sc), a specific component (A) is loaded in the micro-chamber (111) with one side sealed by the transparent layer (120). The specific component (A) herein can include nucleic acid amplification enzyme, dNTP, buffer or a stabilizer in addition to a primer or a probe.

In step d) (Sd), the injection layer (130) is formed to block the inlet part (112) of the micro-chamber (111) containing the specific component (A). Herein, the injection layer (130) is formed to block the inlet part (112) to prevent discharge of inside materials in order to prevent cross-contamination among the specific materials. At this time, a porous material or punchable material is used to provide common reagents containing samples into the micro-chamber (111) at a time.

Figure 14:
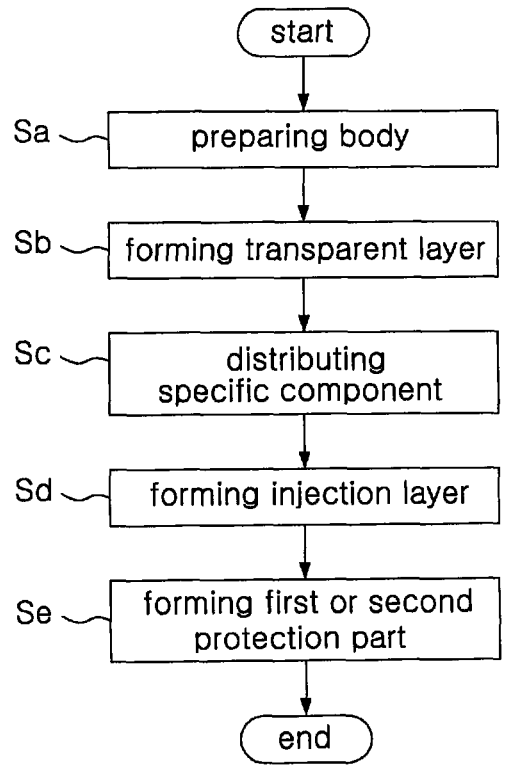
FIG. 14 is a flow chart showing the manufacturing method of the micro-chamber plate of the present invention.

As shown in FIG. 14, the manufacturing method of the micro-chamber plate (100) of the present invention can additionally include the step of e) forming the first protection part (150) protecting the injection layer (130) or the second protection part (160) protecting the transparent layer (120) (Se) after the step of forming the injection layer (130) (Sd).

The manufacturing method of the micro-chamber plate (100) of the present invention can increase analysis efficiency because it does not require a special equipment for distribution such as nano-jet dispenser owing to the injection layer (130) formed on the plate and facilitates fast production of the micro-chamber plate (100) for analysis because it can provide common components without cross-contamination. And the method of the present invention can also reduce the production time for the micro-chamber plate (100) when the pressure regulating device (200) or the rotating device (400) is additionally equipped.

Figure 15:
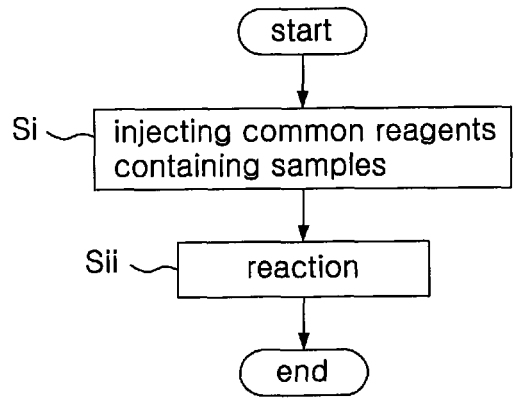
FIG. 15 is a flow chart showing the analysis method using the micro-chamber plate of the present invention.

FIG. 15 is a flow chart illustrating the analysis method using the micro-chamber plate (100) of the present invention. The analysis method using the micro-chamber plate (100) of the present invention uses, as described hereinbefore, the micro-chamber plate (100) and characteristically comprises the following steps: i) injecting common reagents containing samples into the micro-chamber (111) through the injection layer (130) (Si); and ii) reacting the common reagents containing samples with the specific component (A) (Sii).

In the step of injecting common reagents containing samples (Si), the common reagents containing samples are injected into the micro-chamber (111) of the micro-chamber plate (100). If necessary, this step of injecting common reagents containing samples (Si) can be repeated.

In the step of injecting common reagents containing samples (Si), the injection is preferably performed fast under reduced or increased pressure using centrifugal force in order for the common reagents containing samples to be loaded in the micro-chamber (111) efficiently. If the injection layer (130) has the first protection part (150) on its top to protect the injection layer (130), the injection of common reagents containing samples through the injection layer (130) is performed after eliminating the first protection part (150).

In the step of reacting common reagents containing samples (Sii), the common reagents containing samples are reacted with the corresponding specific components (A). In this step (Sii), the reaction is induced by the method selected from the group consisting of PCR (polymerase chain reaction), LCR (ligase chain reaction) and RT-PCR (real time-PCR). PCR).

Real time PCR requires optical measurement process in each cycle during the amplification, unlike the general PCR.

So, if the analysis of a sample using the micro-chamber plate (100) of the present invention is performed with real time PCR, optical measurement (fluorescence assay) is necessary in every cycle, suggesting that an additional step appropriate for each reaction might be added.

Figure 16:
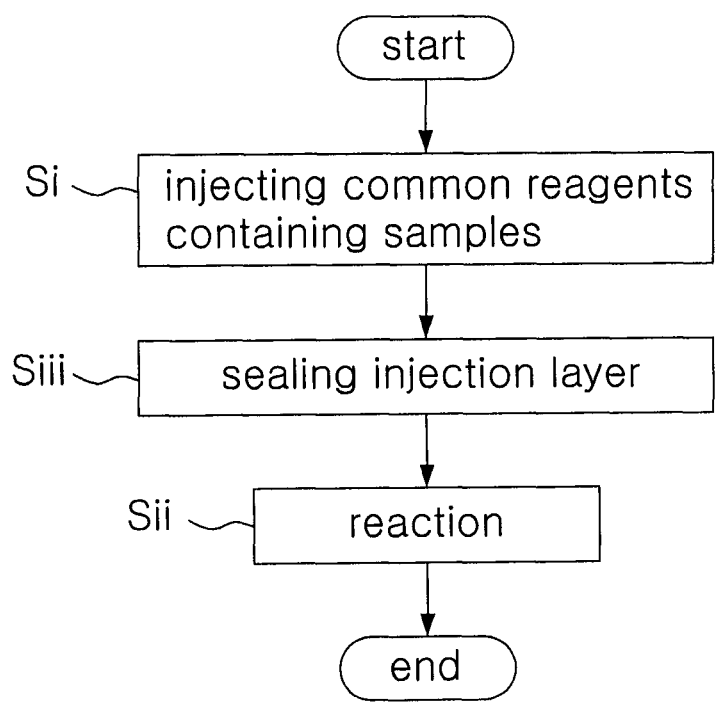
FIG. 16 is another flow chart showing the analysis method using the micro-chamber plate of the present invention.

As shown in FIG. 16, the analysis method of a sample using the micro-chamber plate (100) of the present invention can additionally include the step of iii) sealing the upper part of the injection layer (130) according to the material of the injection layer upon completion of the injection of common reagents containing samples (Siii).

In the step of sealing the injection layer (130) (Siii), the upper part of the injection layer (130) is sealed after the injection of common reagents containing samples. Upon completion of the injection of common reagents containing samples, the injection layer (130) is sealed with an adhesive film, a water-based envelope forming component, oil or a solid component which is a solid at room temperature to maintain the inside status of the micro-chamber (such as condition or status of the mixture of primer or probe, the specific component and the common reagents containing samples).

Figure 17:
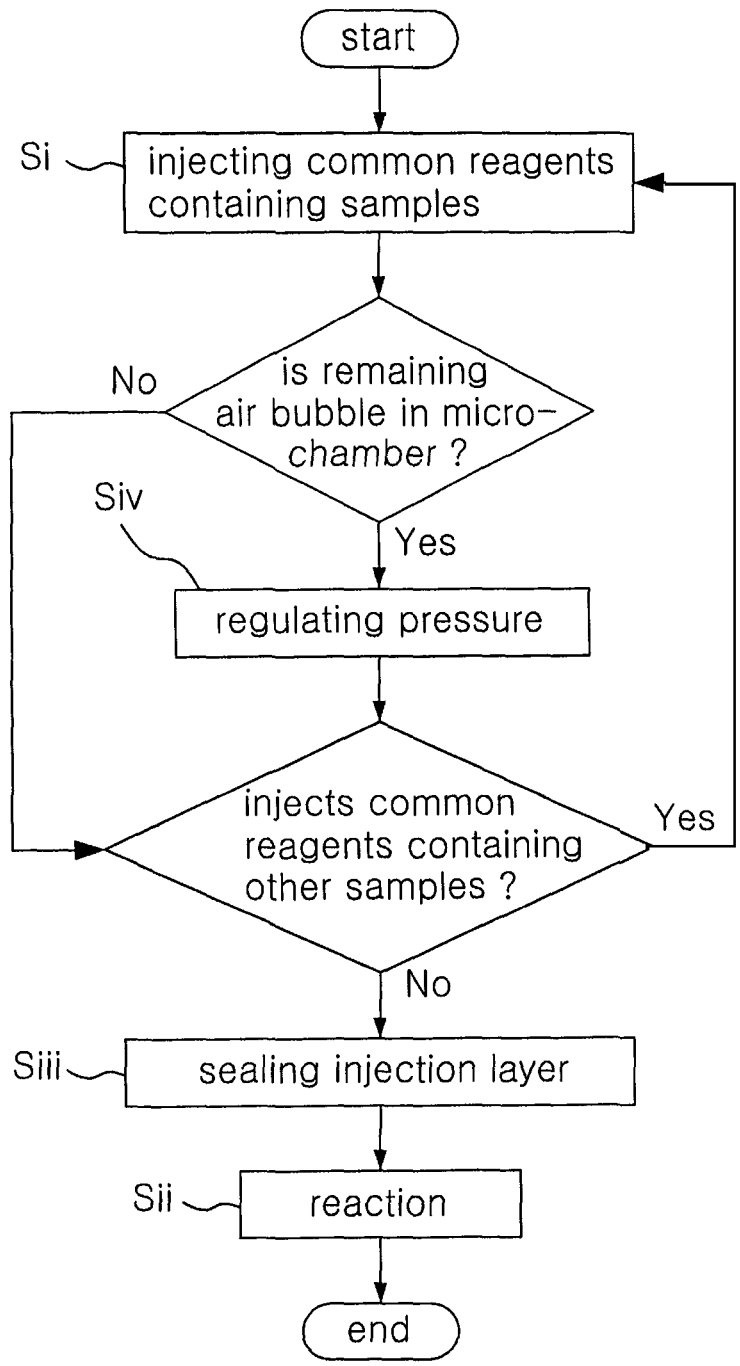
FIG. 17 is another flow chart showing the analysis method using the micro-chamber plate of the present invention.

As shown in FIG. 17, according to the analysis method using the micro-chamber plate (100) of the present invention, if air bubble remains in the micro-chamber (111) without being discharged during the injection of common reagents containing samples, the remaining air bubble scatters light during optical measurement, so that it reduces accuracy of the analysis. Therefore, when multiple samples are injected stepwise with carried in common reagents (Si), the analysis method can additionally include the step of regulating pressure of the micro-chamber plate (100) (Siv) each time upon completion of injection of each sample.

In step of regulating pressure (Siv), reducing pressure-cancellation or increasing pressure is performed to discharge air bubble remaining in the micro-chamber (111) and if necessary this step can be repeated.

Herein, pressure-cancellation or increasing pressure includes all the processes of reducing pressure-cancellation, increasing pressure, reducing pressure-cancellation-increasing pressure.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A micro-chamber plate comprising a body further comprising a plurality of open ended micro-chambers and having an optical measurement part configured for optical measurement on lower side of the body and an inlet part configured for sample injection on upper side of the body; a transparent layer comprising transparent materials and sealing the optical measurement part on lower side of the body; and an injection layer comprising a punchable film or a porous material configured for blocking the inlet part on the upper side of the body for loading common reagents containing samples into the micro-chamber plate, wherein the injection layer is sealed with an adhesive film, a water-based envelope forming component, an oil or a solid component which is a solid at room temperature upon completion of the injection of common reagents containing samples, wherein the micro-chamber plate contains an open space on the upper side by a protrusion of the inlet part area on the body and on top of the injection layer for directly loading common reagents containing samples in the open space to be delivered into the micro-chamber, wherein the micro-chamber plate further comprises a supply layer for gas release and blocking the open space and a supply part on the upper side of the plate for the intake of common reagents containing samples for injecting into multiple micro-chambers simultaneously.

2. The micro-chamber plate according to claim 1, wherein the micro-chamber further comprises a specific component containing a primer or a probe for nucleic acid analysis.

3. The micro-chamber plate according to claim 2, wherein the micro-chamber further comprises a nucleic acid amplification enzyme, dNTP or buffer.

4. The micro-chamber plate according to claim 1, wherein the transparent layer is composed of a material that is not transformed at the temperature of 0° C.-100° C.

5. The micro-chamber plate according to claim 1, wherein the micro-chamber plate is soaked in a separate container filled with common reagents containing samples in order for the common reagents containing samples to be loaded in the micro-chamber.

6. The micro-chamber plate according to claim 1, wherein the micro-chamber is 0.3-3 mm in width.

7. The micro-chamber plate according to claim 6, wherein the micro-chamber is 0.5-5 mm in depth.

8. The micro-chamber plate according to claim 1, wherein the micro-chamber plate additionally contains a first protection part to protect the transparent layer or a second protection part to protect the injection layer.

9. The micro-chamber plate according to claim 8, wherein the first protection part or the second protection part is composed of a separable adhesive film or an attachable material.

10. The micro-chamber plate according to claim 1, wherein the micro-chamber plate is composed of multiple micro-chamber plates as one unit.

11. A manufacturing method of a micro-chamber plate comprising the following steps:
  a) preparing a body having an optical measurement part formed on one side for optical measurement and an inlet part on the other side for sample injection and micro-chambers distinguished one another by multiple open space;
  b) forming a transparent layer on the optical measurement part on the body;
  c) distributing a specific component through the inlet part on the body to load different specific components into the micro-chamber plates; and
  d) forming an injection layer on the other side of the micro-chamber plate wherein the micro-chamber plate made by this method has all the features recited in claim 1.

12. A method for analyzing samples using the micro-chamber plate of claim 1 comprising the following steps:
  i) injecting common reagents containing samples into the micro-chamber through the injection layer of the micro-chamber plate; and
  ii) reacting the common reagents containing samples with the specific components.

13. The method for analyzing samples using the micro-chamber plate according to claim 12, wherein the method additionally includes the step of
  (iii) sealing the upper part of the injection layer upon completion of the injection of common reagents containing samples.

14. The method for analyzing samples using the micro-chamber plate according to claim 12, wherein the step of injecting common reagents containing samples is performed under the effect of centrifugal force and under reduced or increased pressure for efficient injection of the common reagents containing samples into the micro-chamber.

15. The method for analyzing samples using the micro-chamber plate according to claim 12, wherein the method additionally includes the step of (iv) regulating the pressure of the micro-chamber plate in between each injection, if multiple samples are injected stepwise.

16. The method for analyzing samples using the micro-chamber plate according to claim 15, wherein the step of regulating pressure of the micro-chamber plate includes reducing pressure-cancellation or increasing pressure process to discharge air bubbles remaining in the micro-chamber.

\* \* \* \* \*